(12) United States Patent
Gambale et al.

(10) Patent No.: US 6,273,850 B1
(45) Date of Patent: *Aug. 14, 2001

(54) DEVICE FOR POSITIONING A RADIATION SOURCE AT A STENOSIS TREATMENT SITE

(75) Inventors: Richard A. Gambale, Tyngsboro; James Stewart Hunter, Westford; Nareak Douk, Lowell, all of MA (US)

(73) Assignee: Medtronic AVE, Inc., Santa Rosa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/960,375

(22) Filed: Oct. 29, 1997

(51) Int. Cl.[7] ........................................ A61N 5/00
(52) U.S. Cl. ........................................ 600/3; 600/7; 600/8
(58) Field of Search ........................... 600/1–8; 604/27, 604/51, 52, 53, 57, 59, 62, 64, 130; 606/7

(56) References Cited

U.S. PATENT DOCUMENTS

| | | |
|---|---|---|
| 4,763,671 | 8/1988 | Goffinet . |
| 4,819,618 | 4/1989 | Liprie . |
| 5,106,360 * | 4/1992 | Ishiwara et al. ............ 600/2 |
| 5,199,939 | 4/1993 | Dake et al. . |
| 5,213,561 | 5/1993 | Weinstein et al. . |
| 5,282,781 | 2/1994 | Liprie . |
| 5,302,168 | 4/1994 | Hess . |
| 5,354,257 | 10/1994 | Rouin et al. . |
| 5,411,466 | 5/1995 | Hess . |
| 5,484,384 | 1/1996 | Fearnot . |
| 5,498,227 | 3/1996 | Mawad . |

(List continued on next page.)

FOREIGN PATENT DOCUMENTS

| | | |
|---|---|---|
| 1 197 631 | 12/1985 | (CA) . |
| 1065989 | 12/1959 | (DE) . |
| 1095963 | 12/1960 | (DE) . |
| 1466774 | 6/1969 | (DE) . |
| 3620123 A1 | 6/1988 | (DE) . |
| 3643893 A1 | 6/1988 | (DE) . |

(List continued on next page.)

OTHER PUBLICATIONS

*Nuclear Physics,* Chapter 43, Sections 43–2 through 43–8, pp. 1076–1091.

"Low–Dose, β–Particle Emission From 'Stent' Wire Results in Complete, Localized Inhibition of Smooth Muscle Cell Proliferation" by Tim A. Fischell, M.D. et al., *Basic Science Reports,* vol. 90, No. 6, Dec., 1994, pp. 2956–2962.

"Low–Dose, Radioactive Endovascular Stents Prevent Smooth Muscle Cell Proliferation and Neointimal Hyperplasia in Rabbits"by Christoph Hehrlein, M.D. et al., *Basic Science Reports,* vol. 92, No. 6, Sep. 15, 1995, pp. 1570–1575.

"Inhibition of Neointimal Proliferation With Low–Dose Irradiation From a β–Patricle–Emitting Stent" by John R. Laird, M.D. et al., *Basic Science Reports,* vol. 93, No. 3, Feb. 1, 1996, pp. 529–536.

(List continued on next page.)

*Primary Examiner*—Linda C. M. Dvorak
*Assistant Examiner*—R. Kearney
(74) *Attorney, Agent, or Firm*—Sterne, Kessler, Goldstein & Fox PLLC

(57) ABSTRACT

An apparatus is described for irradiating a stenosed region of an artery by use of a sliding or floating radiation source inserted into or onto a catheter or onto a guide wire within a catheter, delivered to the treatment site by a mechanical or hydraulic fluid and housed at the site for the irradiation procedure.

18 Claims, 6 Drawing Sheets

U.S. PATENT DOCUMENTS

| | | |
|---|---|---|
| 5,549,581 | 8/1996 | Lurie et al. . |
| 5,573,509 | 11/1996 | Thornton . |
| 5,618,266 | 4/1997 | Liprie . |
| 5,643,171 | 7/1997 | Bradshaw et al. . |
| 5,683,345 | 11/1997 | Waksman et al. .......... 600/3 |
| 5,728,042 | 3/1998 | Schwager ................. 600/3 |
| 5,730,698 | 3/1998 | Fischell et al. ........... 600/3 |
| 6,024,690 * | 2/2000 | Lee et al. ................. 600/3 |

FOREIGN PATENT DOCUMENTS

| | | |
|---|---|---|
| 3739749 A1 | 6/1989 | (DE) . |
| 0 152 124 | 8/1985 | (EP) . |
| 0 448 004 A2 | 3/1991 | (EP) . |
| 0 448 004 A3 | 3/1991 | (EP) . |
| 0 433 011 A1 | 6/1991 | (EP) . |
| 0 447 745 A2 | 9/1991 | (EP) . |
| 0 447 745 A3 | 9/1991 | (EP) . |
| 0 497 495 A2 | 8/1992 | (EP) . |
| 0 497 495 A3 | 8/1992 | (EP) . |
| 0 593 136 A1 | 4/1994 | (EP) . |
| 0 688 580 A1 | 12/1995 | (EP) . |
| 0 826 393 | 3/1998 | (EP) . |
| 793158 | 4/1958 | (GB) . |
| 1219604 | 1/1971 | (GB) . |
| 1558127 | 12/1979 | (GB) . |
| 57-78654 | 10/1980 | (JP) . |
| 297814 | 10/1969 | (SU) . |
| WO 93/04735 | 3/1983 | (WO) . |
| WO 85/02779 | 7/1985 | (WO) . |
| WO 80/03827 | 4/1990 | (WO) . |

OTHER PUBLICATIONS

"Catheter–Based Radiotherapy to Inhibit Restenosis After Coronary Stenting" by Paul S. Teirstein et al., *The New England Journal of Medicine,* Jun. 12, 1997, vol. 336, No. 24 (one page).

"Restenosis After PTCA Prevented By Radiation Therapy" by Individual, Inc., *Medical Device Business News,* 12–00–96 p. 16.

* cited by examiner

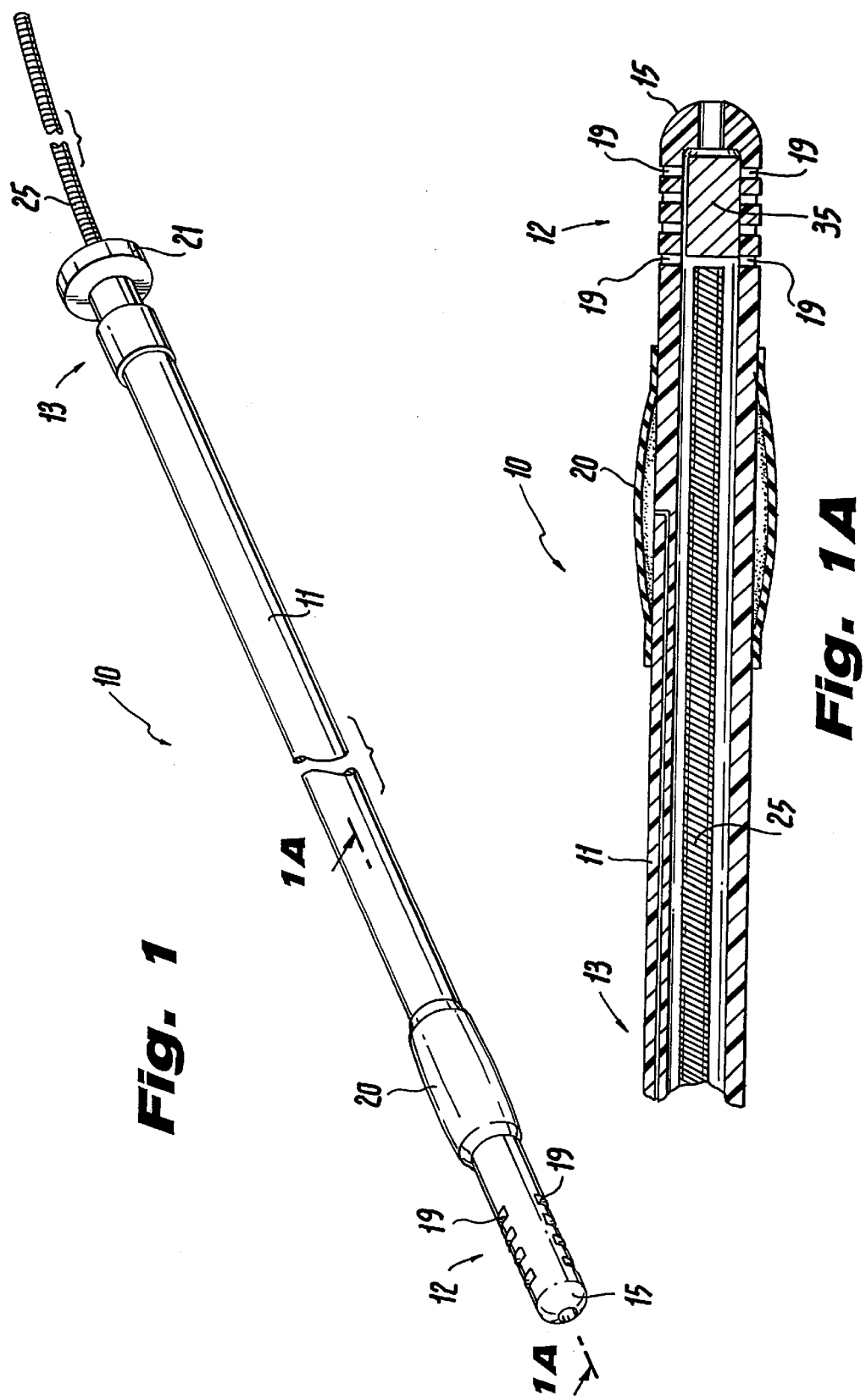

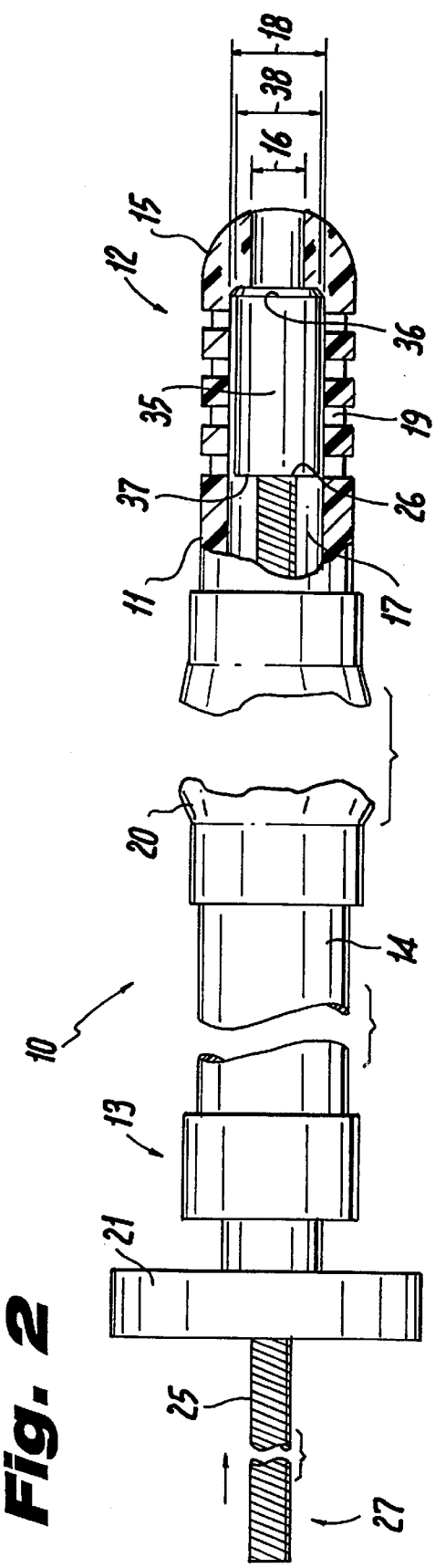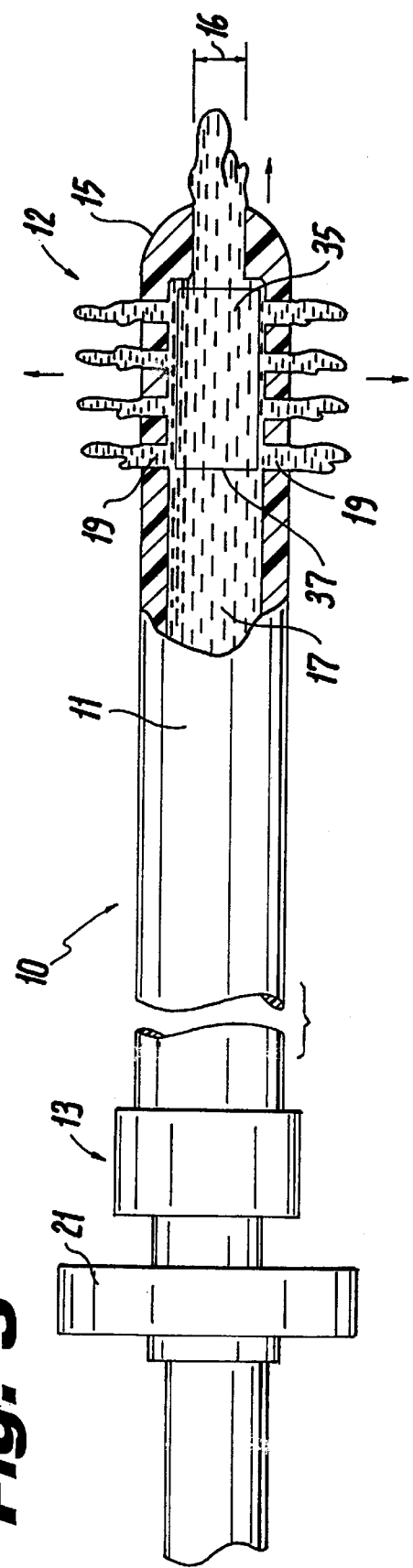

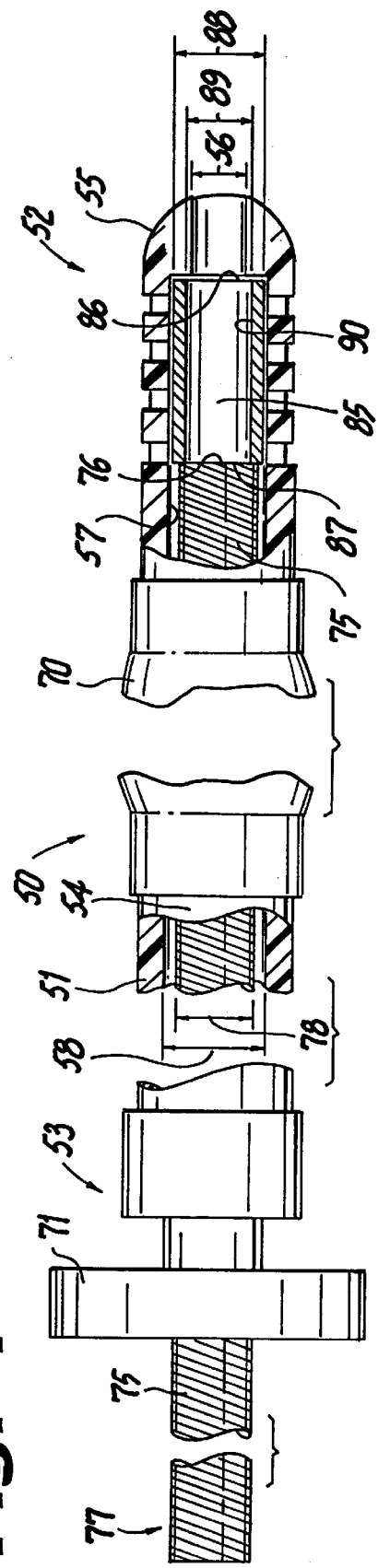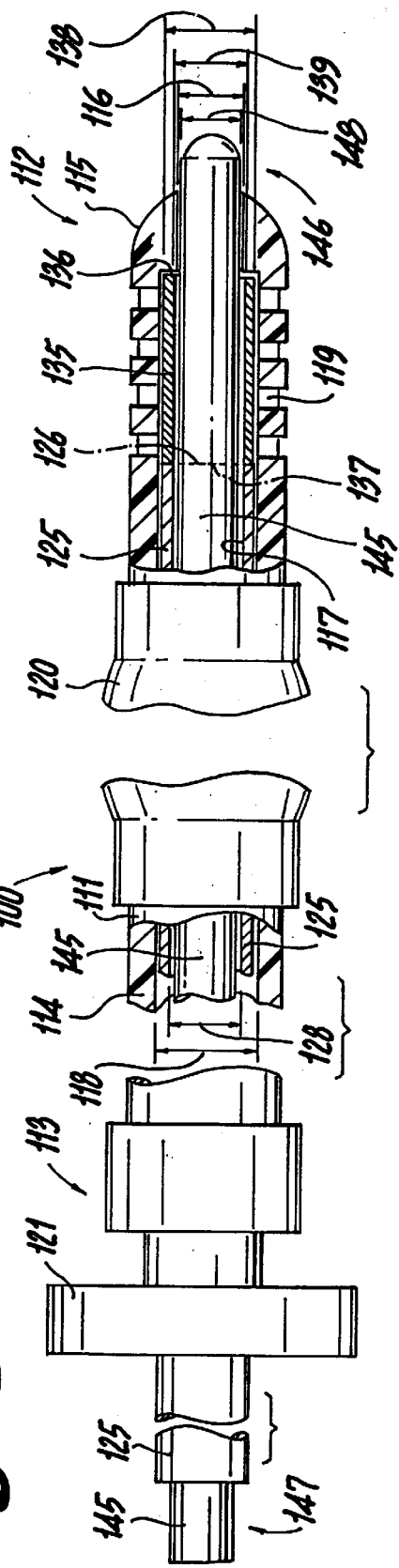

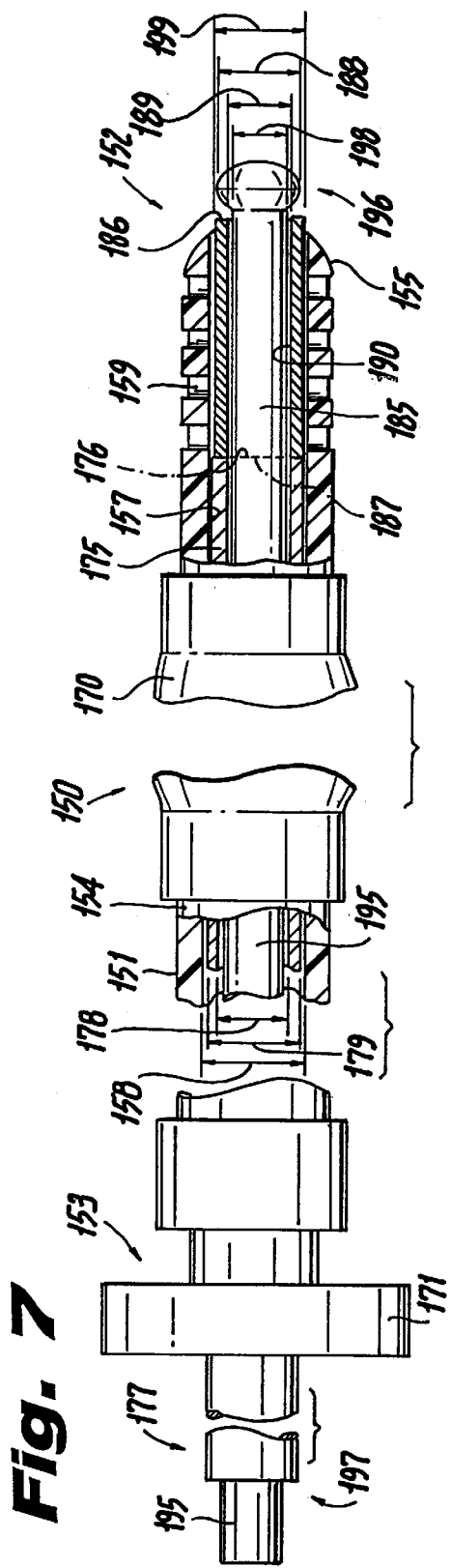
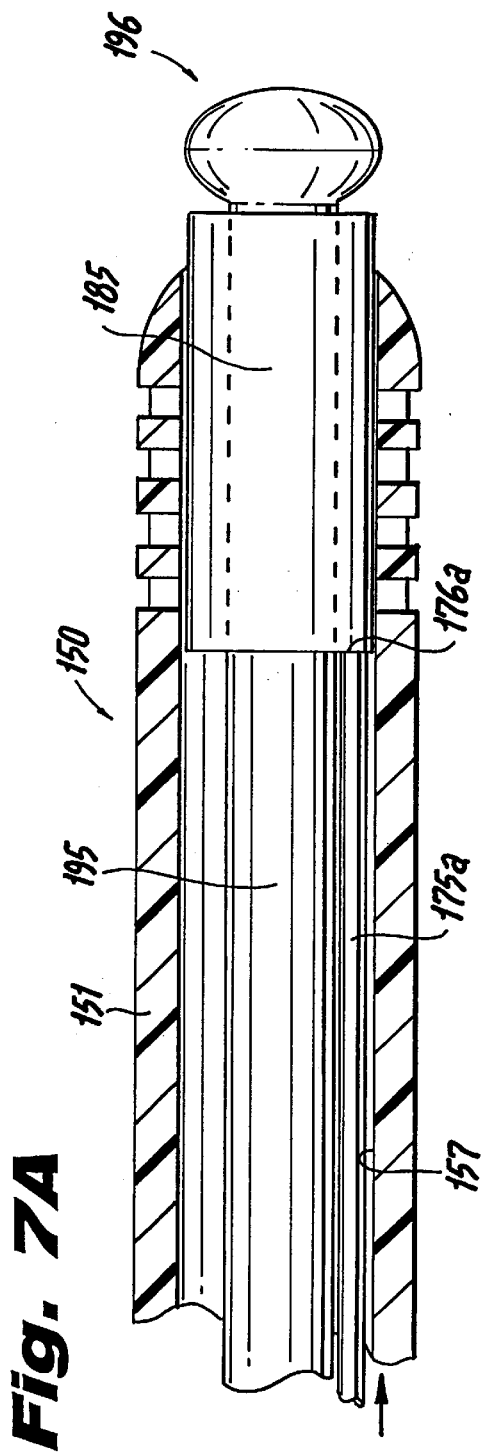
Fig. 7
Fig. 7A

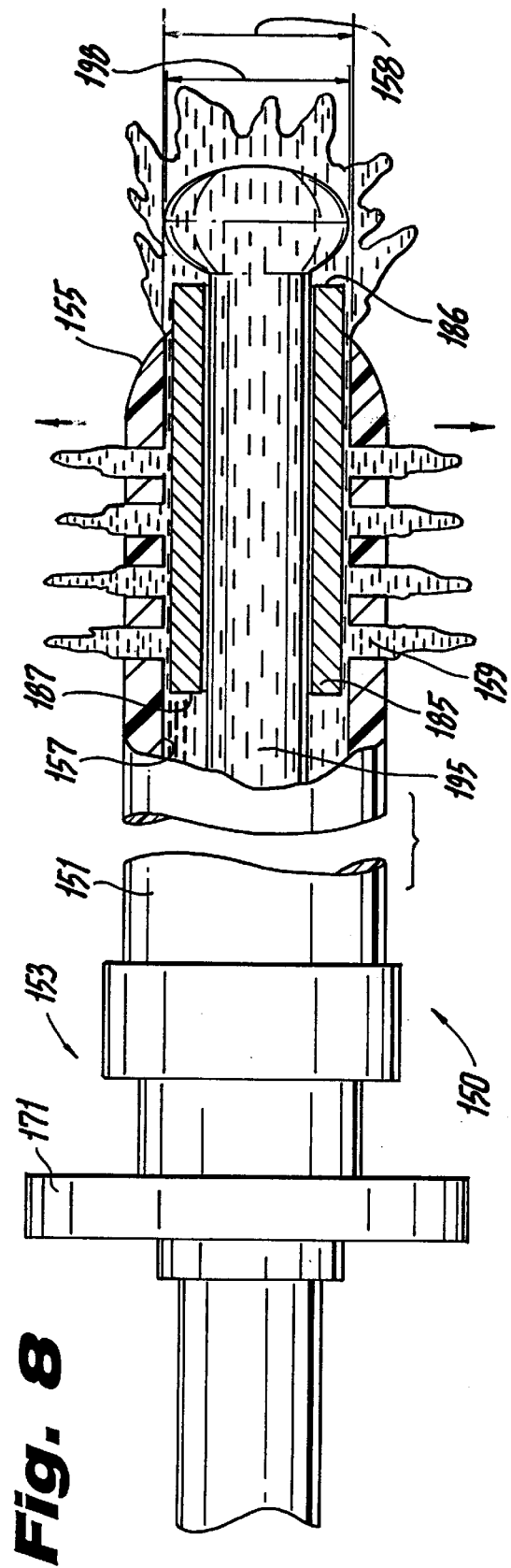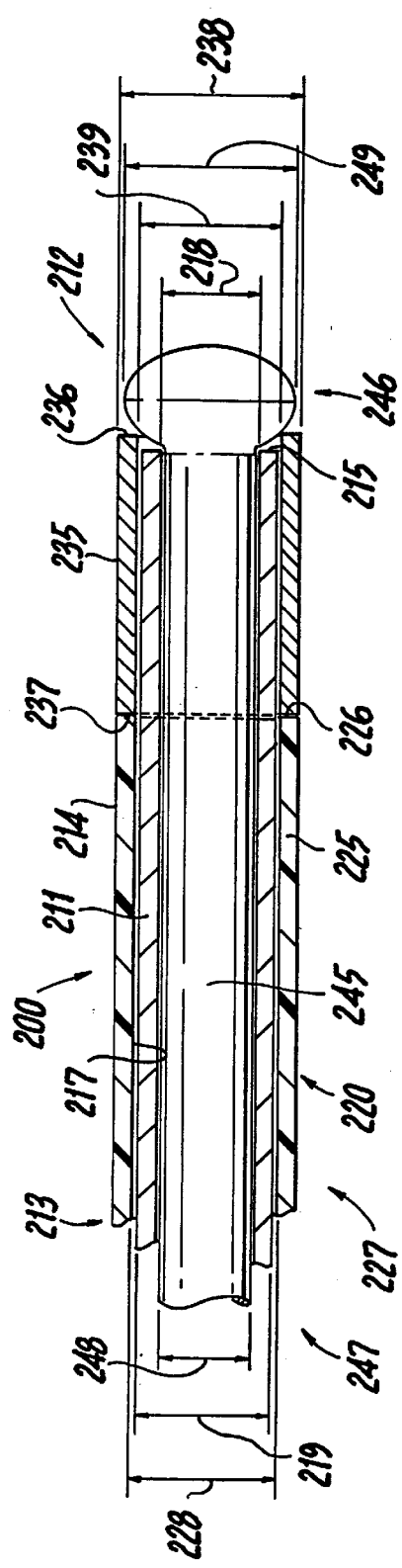

DEVICE FOR POSITIONING A RADIATION SOURCE AT A STENOSIS TREATMENT SITE

BACKGROUND OF THE INVENTION

1. Field of the Invention

This invention generally relates to radiation therapy for treating restenosis. More particularly, this invention relates to a device for irradiating a stenosed region of an artery by means of a radiation source.

2. Brief Description of Related Art

The treatment of restenosis after angioplasty using radiation is well known. Angioplasty (also referred to as percutaneous transluminal angioplasty (PTA)), is a non-surgical technique for unblocking vascular lumens resulting from peripheral and coronary vascular disease. This technique has become an accepted form of treatment in both the United States and internationally. Another form of treating vascular disease is atherectomy, which involves the removal of stenotic lesions from arteries by means of a cutting tool.

In typical angioplasty procedures, a guiding catheter is percutaneously introduced into the vascular system of a patient's body through an artery. Once inserted, the guiding catheter is maneuvered through the vascular artery until the distal tip of the guiding catheter is positioned proximal to the lesion site. A balloon catheter and a guide wire are then introduced through the guiding catheter. First, the guide wire is advanced through the distal tip of the catheter until the distal end of the guide wire moves past the lesion to be dilated. Then, the balloon catheter is advanced over the guide wire to a location such that the balloon is positioned inside the atherosclerotic narrowing of the artery. The angioplasty procedure may then begin by inflating the balloon to a predetermined size, thereby compressing the atheroma. This enlarges the atherosclerotic narrowing and enlarges the lumen by stretching the vessel wall. After a predetermined period of time, the balloon is deflated, completing a portion the procedure.

However, a recurrent problem following angioplasty or atherectomy is that excessive tissue growth may occur at the site of the treated lesion, thereby causing the development of further blockage or renarrowing of the diseased vessel. This problem, called restenosis, is thought to be part of the natural healing process after stretching the vascular structure during angioplasty. It is caused by fibrointimal proliferation of the stretched wall in which the cells lining the vascular interior multiply and form fibrous tissue. Restenosis can result in the necessity of repeating the angioplasty or atherectomy procedure.

The use of radiation therapy to prevent the growth of such fibrous tissue after an angioplastic or atherectomy procedure, thereby reducing the tendency for restenosis, is well known. The following United States Letters Patents disclose various embodiments for such irradiation treatment: U.S. Pat. No. 5,199,939 to Dake et al., U.S. Pat. No. 5,302,168 to Hess, U.S. Pat. No. 5,354,257 to Roubin et al. and U.S. Pat. No. 5,411,466 to Hess, which are incorporated in their entireties herein by reference. The devices in each of the foregoing patents expose a stenosis site to radiation by providing a carrier, e.g., a catheter and/or guide wire, which includes a radiation source and advancing the carrier in order to deliver the radiation source to the treatment site. In addition, the Dake patent discloses the use of a liquid, gas or powder radioactive source separate from a carrier. None of the aforementioned patents teaches delivering the radiation source by first positioning the carrier, then inserting a sliding pellet or sleeve type radiation source into or onto the carrier and applying a mechanical or hydraulic force in order to deliver the source to the stenosis site. Accordingly, for irradiation using a non-liquid or gas radiation source, each of the devices (and the methods for using such devices) taught in the U.S. Patents referenced above necessitate the insertion of a carrier provided with the radiation source.

There are several shortcomings of the prior art devices and methods which we have identified. For example, at the appropriate time for the irradiation procedure, the carrier provided with the radiation source must be precisely placed at the stenosis site. The physician performing the procedure accomplishes such precise placement by maneuvering the proximal end of the carrier in order to move its distal end. The physician views the placement of the carrier using fluoroscopic imaging. With the radiation source permanently provided at the distal end of the carrier, the precise placement of the carrier is critical because should an error occur in placing the radiation, the success of the procedure can be jeopardized, healthy tissue can be improperly irradiated and the length of time to successfully complete the procedure can be increased. More particularly, misplacing the source even slightly from the lesion site can result in improper irradiation of the site since the period of time which the source must remain in place is dependent upon its distance from the lesion site walls. Also, misplacing the source from the lesion site can result in irradiating another segment of the vascular artery, thereby exposing healthy tissue to unnecessary radiation.

Another shortcoming of the prior art devices and methods involves integrating the carrier and the radiation source into one device for use in the procedure. Namely, integrating separate components increases the rigidity of the device. This impacts the physician's ability to track the device through the tortuous arteries because greater rigidity makes maneuvering the device more difficult. Where a malfunction renders either the carrier or the source unusable, the procedure must be interrupted, and a new integrated device must be used. For example, should kinking occur in either the guide wire and/or catheter during insertion into vascular arteries, the entire integrated device may be affected. Kinking of the integrated carrier device can cause the misplacement problems described above and cause the patient to be exposed to the radiation source or an unnecessary period of time. Moreover, where the carrier must be replaced due to kinking or another malfunction, the radiation source will not be used for its intended purpose because it will be discarded along with the catheter. Similarly, where the radiation source is defective, the catheter and/or guide wire is rendered unusable. Accordingly, where these complications occur, the irradiation procedure will be delayed or unsuccessful.

Another disadvantage associated with a device in which a carrier and a radiation source are integrated is that the device must be specially manufactured. Given the number of variations in both catheters and guide wires, adding a radioactive source to such carriers not only increases the manufacturing cost but adds to the complexity of the device which can result in an increase in the cost and complexity of the irradiation procedure itself. Once constructed, the added complexity of the carriers increases the chance that the carrier and/or radiation source will malfunction.

During use, where any of the above malfunctions or complications occurs, the period of time that the radiation source is present in the patient's body as well as the length of time required to successfully complete the irradiation procedure will be increased. This results in increasing the patient's exposure to medical risks inherent in the irradiation procedure as well as more general medical procedure risks.

The likelihood of additional complications for the patient is thereby also increased.

Accordingly, there is a need to improve the devices heretofore known for irradiating a stenosis site, in order to overcome the above described shortcomings in the known devices and methods.

SUMMARY OF THE INVENTION

The present invention is directed to an improved device for delivering, positioning and housing a radiation source at a stenosis site for preventing restenosis. The device involves first positioning a catheter and/or a guide wire precisely at the stenosis site, then inserting a sliding pellet or sleeve type radiation source into or onto the catheter and/or guide wire and applying a mechanical force (e.g., applying forward pressure to a push wire) or hydraulic fluid (e.g., injected saline solution) to deliver and house the source at the stenosis site for the procedure.

The present invention overcomes the shortcomings of known devices and techniques by using a carrier, e.g., a catheter and/or guide wire, and a radiation source which are separate devices. Such nonintegrated devices enable a physician to locate the distal end portion of the carrier precisely at the stenosis site before inserting the radiation source into or onto the catheter. Then, the radiation source may be delivered to the distal end portion of the carrier adjacent to the treatment site. Since the physician can precisely place the carrier before the radiation source is inserted, accurate placement of the source can be facilitated. In addition, the period of time to complete the procedure is streamlined, thereby reducing the risks to which a patient is exposed both by the irradiation procedure and broader medical risks.

We have also determined that with the present invention, the use and manufacture of the carrier and radiation source is simplified and less expensive. A single radiation source can be designed to be compatible with a variety of catheters. This reduces the number of separate catheters, guide wires and radiation sources which must be maintained in inventory and, accordingly, the inventory size. Moreover, individual radiation sources are significantly more compact than an integrated carrier and radiation source. As a result, they are appreciably easier to store, isolate and dispose of than a larger integrated device. In addition, due to greater simplicity of the present invention, the chance of malfunctions during the procedure is reduced. Similarly, where a malfunction of one of the parts of this invention (e.g., the carrier or the radiation source) occurs, the other part is unaffected and may continue to be used for the procedure. Thus, replacement due to a failure of any part in the present invention is easier, less expensive and more safe than where the carrier and radiation source are integrated into one device.

These and other features and advantages of the invention will be readily apparent from the following detailed description of certain embodiments taken in conjunction with the accompanying unscaled drawings.

BRIEF DESCRIPTION OF THE DRAWING

FIG. 1 is a perspective view of a catheter and a push wire constructed according to this invention;

FIG. 1A is an enlarged longitudinal sectional view of the catheter and the push wire of FIG. 1 taken along the line 1A—1A, and a radiation source constructed according to this invention;

FIG. 2 is an enlarged longitudinal sectional view of a distal end portion of the catheter, the push wire and the radiation source of FIG. 1 constructed according to this invention;

FIG. 3 is an enlarged longitudinal sectional view of the distal end portion of the catheter and the radiation source of FIG. 1 constructed according to a first alternative embodiment of this invention;

FIG. 4 is an enlarged longitudinal view of a distal end portion of a catheter, a push wire and a radiation source constructed according to a second alternative embodiment of this invention;

FIG. 5 is an enlarged longitudinal view of a distal end portion of a catheter, a guide wire, a push wire and a radiation source constructed according to a third alternative embodiment of this invention;

FIG. 7 is an enlarged longitudinal view of a distal end portion of a catheter, a guide wire, a push wire and a radiation source constructed according to a fifth alternative embodiment of this invention;

FIG. 7A is an enlarged longitudinal sectional view of a distal end portion of a catheter and the radiation source of FIG. 7 and an alternative embodiment of the push wire constructed according to this invention;

FIG. 8 is an enlarged longitudinal sectional view of the distal end portion of the catheter, the guide wire and the radiation source of FIG. 7 constructed according to a sixth alternative embodiment of this invention; and FIG. 9 is an enlarged longitudinal sectional view of a distal end portion of a catheter, a guide wire and a radiation source constructed according to a seventh alternative embodiment of this invention.

DETAILED DESCRIPTION OF A PREFERRED EMBODIMENT

Figure 5A:
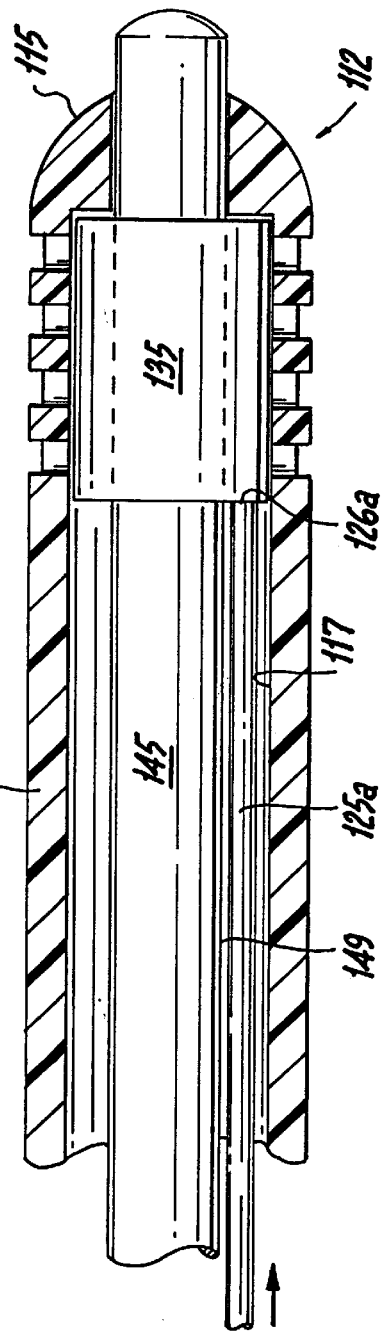
FIG. 5A is an enlarged longitudinal sectional view of the distal end portion of the catheter and the radiation source of FIG. 5 and an alternative embodiment of the push wire constructed according to this invention.

By way of overview and introduction, FIG. 1 is a perspective view of an irradiation device 10 constructed according to this invention. FIG. 1A is an enlarged longitudinal sectional view of the irradiation device 10 of FIG. 1 taken along the line 1A—1A. The irradiation device 10 shown in FIGS. 1 and 1A generally comprises a balloon catheter 11 (hereinafter, the catheter 11), which can be a conduit for the delivery of a radiation source 35 to a distal end portion 12 of the catheter 11. The distal end portion 12 can be maneuvered to the stenosed region just prior to delivery of the radiation source 35. After placing the radiation source 35 into a proximal end portion 13 of the catheter 11, a push wire 25 (which can be, e.g., a guide wire) can be inserted into the catheter 11 to abut the radiation source 35. A mechanical force can then be applied to the push wire 25 in the distal direction and translated to the radiation source 35 in order to deliver the radiation source 35 through the catheter 11 to the distal end portion 12. The distal end portion 12 can be a housing for the radiation source 35 in order to irradiate the stenosis site.

The irradiation device 10 constructed according to this invention can be utilized in the following manner: the stenosed region of an artery is identified using an appropriate diagnostic procedure. Such procedures are well known in the art and are not described further herein. In the event that angioplasty is indicated, the physician makes a small incision in the body to gain access to a vascular pathway. An introducer, including a short tapered tube with a proximal fitting, is then placed in the incision to act as an initial guiding device and entry point for additional devices placed into the pathway.

A guide wire is then maneuvered into and advanced through the vascular pathway to a location past the stenosis or treatment site. The guide wire or other device including, e.g., the catheter 11 or the push wire 25, are imaged using fluoroscopy while being advanced through the pathway. In this way, the physician has a visual means of tracking the precise location of such devices. Then, the catheter 11, including a balloon 20 which is deflated, is threaded over the guide wire and advanced so that the balloon 20 is positioned precisely at the stenosis site. The physician uses the proximal end portion 13 of the catheter 11 to position the balloon 20 at the precise location. Once the catheter 11 is verified to be in position using fluoroscopy imaging, the balloon 20 can be inflated to start the angioplasty procedure. The balloon 20 remains in that position and is inflated and deflated one or more times to widen the constricted area.

At the appropriate time for the irradiation procedure, the catheter 11 is repositioned so that the distal end portion 12 is located precisely at the stenosis site. The physician again uses the proximal end portion 13 to position the distal end portion 12 at that location. With the catheter 11 in place, the radiation source 35 is inserted into the catheter 11 from a luer fitting 21.

The push wire 25 can then be inserted into the luer fitting 21 for the purpose of directing the radiation source 35 to the distal end portion 12. The physician can then apply forward pressure to the push wire 25 in the distal direction. Such forward pressure causes the push wire 25 to abut the radiation source 35. Additional forward pressure on the push wire 25 is translated to the radiation source 35 in order to move the radiation source 35 from the proximal end portion 13 to the distal end portion 12 of the catheter 11. In this way, the push wire 25 allows the physician to apply a mechanical force to the radiation source 35.

The distal end portion 12 includes a distal end 15 which can be partially closed wall. The distal end 15 enables the catheter 11 to act as a housing for the radiation source 35. The distal end portion 12 further contains a series of vents 19 which allow for irradiation of the vascular walls when the radiation source 35 is in the distal end portion 12.

The radiation source 35 acts on the treatment site for a specific period of time. Such period depends on the strength of the radiation source 35 and the distance between the radiation source 35 and the walls.

Upon completion of the specified time period for irradiating the stenosis site, the radiation source 35 can be removed from the vascular pathway by withdrawing the catheter 11 along with the push wire 25. The distal end 15 of the catheter 11 can house the radiation source 35 during and after removal from the pathway.

The invention can also be used with a catheter which does not include a balloon (not shown). In this embodiment, the balloon catheter used for the angioplasty procedure can be removed before inserting a catheter without a balloon. The catheter without a balloon is then equivalent to the balloon catheter 11 for the delivery and housing functions of the irradiation device 10.

Having described the general use of the irradiation device constructed according to this invention, it is now described in greater detail. Referring to FIG. 2, the catheter 11 is a flexible elongated tube 14 having the distal end portion 12, the proximal end portion 13, and a passageway or lumen 17 extending longitudinally therebetween and having a diameter 18. The diameter 18 is also equivalent to the inner diameter of the tube 14. In this embodiment, the catheter 11 is a carrier for the radiation source 35. The radiation source 35 has a diameter 38 which is smaller than the diameter 18 of the lumen 17. The push wire 25 is a flexible elongated wire or tube (e.g., a wire is shown in FIG. 2) composed of metal or plastic and having a distal end 26 and a proximal end portion 27.

As to the catheter 11, the distal end portion 12 also includes the distal end 15 which is directable through the vascular pathway. In addition, the distal end 15 comprises a wall extending from the distal end of the tube 14. In this embodiment, the distal end 15 does not form a closed end of the catheter 11. Rather, there is a aperture in the wall of the distal end 15, the aperture having a diameter 16 which is smaller than the diameter 18 of the lumen 17. The radiation source 35 has the diameter 38 which is smaller than the diameter 18 of the lumen 17 but larger than the diameter 16 of the aperture of the distal end 15. Accordingly, the distal end 15 acts as an impediment to movement of the radioactive source 35 past such distal end 15. In this way, the distal end 15 enables the catheter 11 to house the radiation source 35 at the distal end portion 12.

In an alternative embodiment according to this invention, the distal end 15 can be closed (not shown). In this embodiment, the distal end 15 serves the same purpose as such distal end 15 containing an aperture because the it impedes movement of the radiation source 35 past the distal end portion 12. Also, in further embodiments, there may be an inward protrusion in the lumen 17 (not shown), which sufficiently narrows the diameter 18 of the lumen 17 to impede movement of the radiation source 35 beyond such protrusion. The inward protrusion can be located either at the distal end 15 or anywhere within the lumen 17. Accordingly, our invention includes any mechanism, whether a protrusion constructed as an integral part of or added to the lumen 17 or the distal end 15, which impedes the radiation source 35 from moving past it.

Where an angioplasty procedure has been performed and the irradiation procedure is indicated, the catheter 11 can be relocated so that the distal end portion 12 of the catheter 11 is placed precisely at the stenosis site. The proximal end portion 13 is used by the physician to precisely place the distal end portion 12. The distal end portion 12 further includes a series of vents 19 which allow the radiation source 35 to irradiate the treatment site.

In an alternative embodiment of the present invention, the distal end portion 12 including the vents 19 can be located at a greater distance proximal to the distal end 15 than is illustrated in FIG. 2. For example, the area in which the radiation source 35 is housed (e.g., the distal end portion 12 in FIG. 2) can be within the balloon 20. A wall or protrusion may be added within the lumen 17 just distal to the balloon 20 to impede the radiation source 35 from moving past the protrusion. In another alternative embodiment, the balloon 20 can be relocated to the distal end portion 12 over the vents 19. In this way, both the balloon 20 and the distal end portion 12 which houses the radiation source 35 are placed at the treatment site during a single placement of the catheter 11. Accordingly, with these alternative embodiments, when the angioplasty procedure is completed, the irradiation procedure can begin without the need for the physician to relocate the portion of the catheter 11 where the radiation source 35 is to be housed at the treatment site.

In a further alternative embodiment, the irradiation treatment can be applied by an irradiation catheter (not shown)

separate from the balloon catheter 11. In this embodiment, the balloon catheter 11 is removed after the angioplasty procedure, leaving the guide wire in place. The irradiation catheter is advanced distally to the stenosis site over the wire. The guide wire can than be removed according to the particular embodiment of the present invention. The radiation source 35 can thereafter be inserted into the irradiation catheter and advanced, for example, by the push wire 25 to the stenosis site.

In the embodiment shown in FIG. 2, the radioactive source 35 is a cylindrically shaped solid pellet. In addition, any solid shape for the radioactive source 35 having a cross section sufficiently small to fit within the diameter 18 of the lumen 17 is contemplated as within the present invention.

The radiation source 35 can be composed of any type of radiation presently known or hereinafter discovered since any radioactive composition for use in the irradiation procedure is contemplated as within the present invention. Examples of presently available gamma type radiation sources are cesium 137, cobalt 60, iodine 125, iodine 131, cobalt 57, iridium 192, gold 198, palladium 103 etc.

After the radiation source 35 is inserted into the catheter 11 at the luer fitting 21, the push wire 25 can then be inserted into the luer fitting 21. The push wire 25 can be a guide wire or other wire or tube having a diameter sufficiently small to fit within the diameter 18 of the lumen 17. The push wire 25 acts to move the radiation source 35 when a forward pressure in the distal direction is applied to the proximal end portion 27 of the push wire 25. Such forward pressure causes the distal end 26 of the push wire 25 to abut a proximal end 37 of the radiation source 35. Additional forward pressure on the push wire 25 translates to the radiation source 35, causing the radiation source 35 to move through the lumen 17 to the distal end portion 12 of the catheter 11.

Maneuvering the push wire 25 with the distal end 26 abutting the proximal end 37 of the radiation source 35 advances such radiation source 35 to the distal end portion 12 until the radiation source 35 is in proximity to the distal end 15. Accordingly, the distal end 15 enables the catheter 11 to act as a housing for the radiation source 35 because a distal end 36 of the radiation source 35 abuts (or is just proximal to) the distal end 15. The distal end 15 thereby prevents the radiation source 35 from moving past the distal end 15 into the vascular pathway. In addition, the proximal end 37 of the radiation source 35 abuts or is just distal to the distal end 26 of the push wire 25. Accordingly, the radiation source 35 is further housed at the distal end portion 12.

With the radiation source 35 in place in the distal end portion 12, the stenosis site is irradiated due to exposure to the radiation source 35 through the vents 19. The radiation source 35 remains in position for a specified period of time. The length of time depends on the distance between the radiation source 35 and the inner blood vessel walls. Presently used treatment times are between about three minutes to about thirty to forty minutes. This time period is gaged according to the dosage of presently available radiation sources and could change considerably based on the use of different radiation sources.

Upon completion of the radiation treatment, the radiation source 35 is removed from the vascular pathway by removing the catheter 11 along with the push wire 25. During removal, the distal end 36 can abut the distal end 15 and the proximal end 37 can abut the distal end 26 of the push wire 25. In this way, the radiation source 35 can remain housed in the distal end portion 12 during the removal of the irradiation device 10 from the body.

Referring to FIG. 3, in a first alternative embodiment of the irradiation device 10 according to this invention, a hydraulic force rather than the mechanical force applied by the push wire 25 (of FIGS. 1 and 2) can be used to deliver the radiation source 35 through the lumen 17. For example, an injection of saline solution can be applied to the lumen 17 at the luer fitting 21 after the radiation source 35 has been inserted into the catheter 11. The force of the injected saline solution on the proximal end 37 of the radiation source 35 causes it to move from the proximal end portion 13 to the distal end portion 12 of the catheter 11.

Moreover, the solution for applying the hydraulic force can exit the catheter 11 at the vents 19 and the aperture in the distal end 15. This is because the diameter 16 of the distal end 15 can be adapted to allow the fluid to exit the catheter 11. The diameter 16 can also be adapted to capture the radiation source 35 and retain it at the distal end portion 12. The solution used to apply the hydraulic force may be any type of solution presently known or hereinafter discovered which is suitable for use in an irradiation treatment. Examples of presently known solutions are saline, or mixtures of saline and radiographic dyes which are used in fluoroscopy to delineate vascular arteries.

The first alternative embodiment of FIG. 3 may also include the push wire 25 (not shown), in addition to the hydraulic force. The push wire 25 can function in a manner identical to such wire of the FIGS. 1 and 2 embodiments. In this way, both mechanical and hydraulic forces can be applied to the radiation source 35.

As to the parts of the irradiation device 10 which are not specifically described regarding FIG. 3, they are equivalent to the embodiments of FIGS. 1 and 2 as to their functions and manner of use (including any alternative embodiments of any part of the irradiation device 10 of FIGS. 1 or 2).

Referring to FIG. 4, illustrated is an irradiation device 50 as a second alternative embodiment according to this invention. The irradiation device 50 comprises a balloon catheter 51 (hereinafter, the catheter 51), a push wire 75 and a radiation source 85. The catheter 51 is a flexible elongated tube 54 including a distal end portion 52, a proximal end portion 53 and a passageway or lumen 57 with a diameter 58 extending longitudinally therebetween. The distal end portion 52 includes a distal end 55. The catheter 51 further includes a balloon 70 and a luer fitting 71. In this embodiment, the catheter 51 is a carrier for the radiation source 85.

A difference between the embodiment of FIG. 4 and the preceding embodiments of FIGS. 1 to 3 is the radiation source 85. The radiation source 85 is a solid sleeve having a proximal end 87 and a distal end 86. The radiation source 85 has an outside diameter 88 which is smaller than the diameter 58 of the lumen 57 and, where the distal end 55 contains an aperture with a diameter 56, the outside diameter 88 is larger than the diameter 56. The radiation source also has a lumen 90 with a diameter equivalent to an inner diameter 89 of the radiation source 85.

In an alternative embodiment, the radiation source 85 can be a partial sleeve composed of a radioactive material wrapped in a circular or spiral fashion but which need not form a complete cylinder. In addition, in further alternative embodiments, the radiation source 85 can be any shape or form, whether symmetrical or amorphous, so long as such shape or form fits within the lumen 57 of the catheter 51 and is constructed to respond to the application of a mechanical force by the push wire 75 and the impedance of the distal end 55.

The push wire 75 is a flexible elongated wire or tube (e.g., a wire is shown in FIG. 4) having a distal end 76 and a proximal end portion 77. The push wire 75 has a diameter 78 sufficiently small to fit within the diameter 58 of the lumen 57. Regardless of whether the push wire 75 is a wire or tube, it is constructed to abut the cross section of the proximal end 87 without slipping over the radiation source 85 or inside the lumen 90. In this way, the push wire 75 can translate a mechanical force applied to it to the radiation source 85. Accordingly, the push wire 75 can interact with the radiation source 85 to advance the radiation source 85 to the distal end portion 52.

The distal end portion 52 of the catheter 51 also includes a distal end 55 having a aperture with a diameter 56. The distal end 86 and the proximal end 87 of the radiation source 85 interact with the distal end 55 of the catheter 57 and the distal end 76 of the push wire 75, respectively, in the same way as the distal end 36 and proximal end 37 interact with the distal end 15 and the distal end 26 (of FIGS. 1 and 2), respectively. In this way, the distal end 55 serves to impede the radiation source 85 from moving past such end 55 of the catheter 51.

Another difference between the embodiment of FIG. 4 and the preceding embodiments of FIGS. 1 to 3 is that the catheter 51 does not include a series of vents at its distal end portion 52. In this embodiment, the catheter 51 and/or the radiation source 85 can be designed such that vents are not needed in order to irradiate the lesion site. The use of vents is dependent on the type and intensity of radiation. For example, Gamma Radiation penetrates polymeric catheter material regardless of the presence or absence of vents. On the other hand, metallic material can provide some shielding such that vents can be used. Also, Beta Radiation, having less energy than Gamma Radiation, is decreased by the presence of material of much less density between a catheter and the lesion site. Accordingly, vents can be used. Moreover, the catheter 51 can be designed with materials and thicknesses (as well as the geometry of the vents in alternative embodiments) for a specific type of radiation. Therefore, the use of vents is a matter of preference based on the design parameters of the catheter and radiation, and does not limit the present invention.

As to the parts of the irradiation device 50 which are not specifically described regarding FIG. 4, they are equivalent to the embodiments of FIGS. 1 and 2 as to their functions and manner of use (including any alternative embodiments of any part of the irradiation device 10 of FIGS. 1 or 2).

Referring to FIG. 5, there is illustrated an irradiation device 100 as a third alternative embodiment according to this invention. The irradiation device 100 comprises a catheter 111 (hereinafter, the catheter 111), a guide wire 145, a push tube 125 and a radiation source 135. The catheter 111 is a flexible elongated tube 114 including a distal end portion 112, a proximal end portion 113 and a passageway or lumen 117 with a diameter 118 extending longitudinally therebetween. The distal end portion 112 includes a distal end 115 having a aperture with a diameter 116. The catheter 111 can further include a series of vents 119, a balloon 120 and a luer fitting 121. In this embodiment, the catheter 111 and/or the guide wire 145 are carriers for the radiation source 135.

A difference between the embodiment of FIG. 5 and the preceding embodiments of FIGS. 1 to 4 is the addition of the guide wire 145. The guide wire 145 is a flexible elongated wire or tube (for example, a wire is shown in FIG. 5) composed of metal or plastic and having a distal end portion 146 and a proximal end portion 147. In addition, the guide wire 145 has a diameter 148 (or, alternatively, where the guide wire 145 is a tube an outer diameter 148) which is smaller than the diameter 118 of the lumen 117 and smaller than the diameter 116 of the aperture in the distal end 115.

Prior to beginning the irradiation treatment, the guide wire 145 can be inserted into the luer fitting 121 of the catheter 111. The physician can use the proximal end portion 147 to maneuver the distal end portion 146 to the vicinity of the distal end 115 (e.g., proximal to, within or through the aperture of the distal end 115). Once the guide wire 145 is in place, the guide wire 145 and the catheter 111 can function to deliver and house the radiation source 135 to the distal end portion 112. Accordingly, the guide wire 145 can be in place in the catheter 111 before the radiation source 135 is delivered. Alternatively, the radiation source 135, can be in place on the guide wire 145 before the guide wire 145 is inserted into the catheter 111.

The radiation source 135 is a sleeve having an inner diameter 139 that is larger than the diameter 148 of the guide wire 145 and an outer diameter 138 which is smaller than the diameter 118 of the lumen 117. The radiation source 135 can be a closed sleeve (as shown in FIG. 5) which is placed on and encircles the guide wire 145. In addition, the radiation source 135 can be constructed according to any of the alternative embodiments described as to the radiation source 85. In another alternative embodiment, the radiation source 135 can include a break in its wall along its longitudinal axis to enable the radiation source 135 to wrap around the guide wire 145.

The push tube 125 can be a tube having an inner diameter 128 which is larger than the outer diameter 148 of the guide wire 145 and smaller than the diameter 118 of the lumen 117. The push tube 125 can be placed over the guide wire 145 either before or after inserting the guide wire 145 into the catheter 111 and either before or after the radiation source 135 is in place on the guide wire 145 (e.g., the radiation source 135 can be added last where it is in the form of a wrap around sleeve or spiral). Once the push tube 125 and the radiation source 135 are in place, a mechanical force can be applied to the push tube 125 to cause it to abut and then move the radiation source 135 to the distal end 112.

The radiation source 135 has a distal end 136 and a proximal end 137, which interact with the distal end 115 of the catheter 111 and a distal end 126 of the push tube 125, respectively, in the same way as the distal end 86 and proximal end 87 of the radiation source 85 interact with the distal end 55 and the distal end 76 (of FIG. 4), respectively.

As to the parts of the irradiation device 10 which are not specifically described regarding FIG. 5, they are equivalent to the embodiment of FIG. 4 as to their functions and manner of use (including any alternative embodiments of any part of the irradiation device 50 of FIG. 4).

In a further alternative embodiment, the diameter 148 of the guide wire 145 and the outer diameter 138 of the radiation source 135 can be sufficiently small, and the diameter 116 of the aperture of the distal end 115 sufficiently large such that absent the guide wire 145, the radiation source 135 can move past the distal end 115. In this embodiment, the distal end portion 146 of the guide wire 145 should be located in the vicinity of the aperture of the distal end 115 (i.e., proximal to, within or through the distal end 115) in order to prevent the radiation source 135 from moving past the distal end 115. While the distal end portion 146 can come into contact with the distal end 115, the distal end portion 146 can impede movement of the radiation source 135 by being placed close enough (without contact)

to the distal end 115 so as to block movement of the radiation source 135 through the aperture of the distal end 115.

Referring to FIG. 5A, there is an alternative embodiment of the irradiation device 100 according to this invention. The push wire 125a can be a rod having a diameter sufficiently small to fit in the space between the lumen 117 of the catheter 111 and an outer wall 149 of the guide wire 145 at any point around the circumference of such wire 145. In this embodiment, the guide wire 145 can also act to impede the push wire 125a from passing through the inner diameter 139 (shown in FIG. 5) of the radiation source 135. In this way, the guide wire 145 assists the push wire 125a in translating a force applied in the distal direction to the radiation source 135, in order to advance the radiation source 135. In addition, the push wire 125a has a diameter that is sufficiently large to abut the radiation source 135. The push wire 125a includes a distal end 126a, which interacts with the radiation source in the same manner as the distal end 126 of the push tube 125. Accordingly, the push wire 125a functions and is used in the same manner as the push tube 125 of FIGS. 4 and 5 described above.

Figure 6:
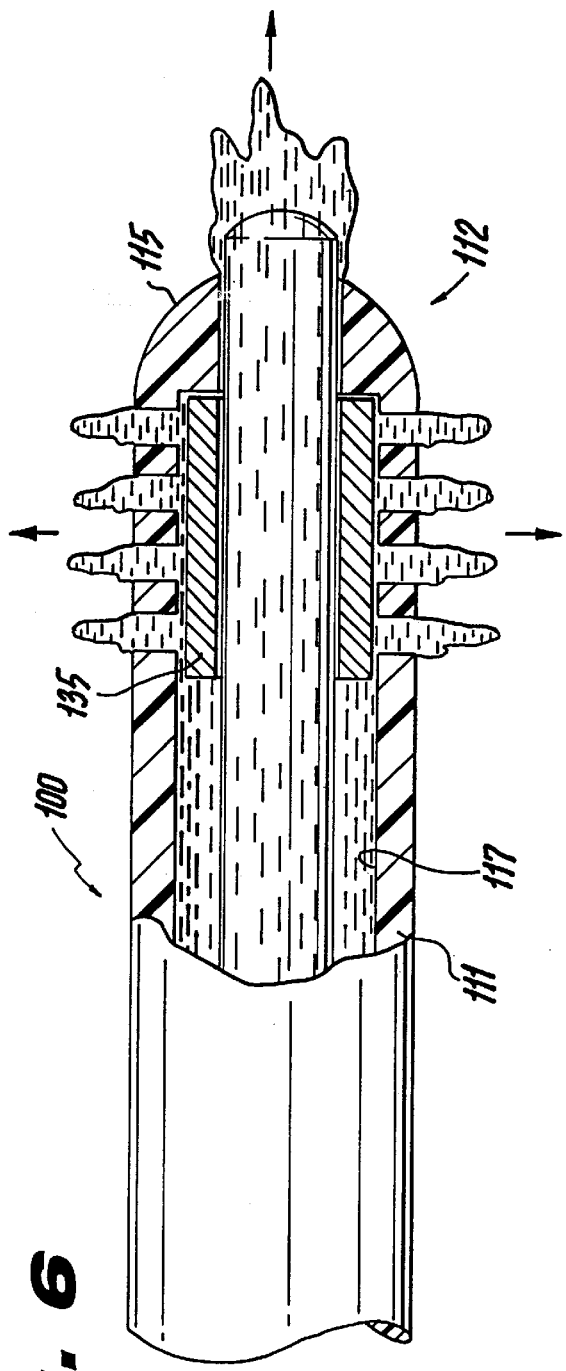
FIG. 6 is an enlarged longitudinal sectional view of the distal end portion of the catheter and the radiation source of FIG. 5 constructed according to a fourth alternative embodiment of this invention.

Referring to FIG. 6, in a fourth alternative embodiment of the irradiation device 100 according to this invention, a hydraulic force can be used to deliver the radiation source 135 to the distal end 115. For example, an injection of saline solution can be applied to the lumen 117 of the catheter 111 after the radiation source 135 has been inserted into the catheter 111. The hydraulic force of the injected saline solution on the proximal end 137 of the radiation source 135 causes the radiation source 135 to move to the distal end portion 112. Moreover, the solution for applying the hydraulic force can exit the catheter 111 at the aperture in the distal end 115.

As to the parts of the irradiation device 100 which are not specifically described regarding FIG. 6, they are equivalent to the embodiments of FIGS. 5 and 5A as to their functions and manner of use (including any alternative embodiments of any part of the device 100 of FIGS. 5 or 5A, including the addition of the push tube 125 or push wire 125a to combine a mechanical force with the hydraulic force).

Referring to FIG. 7, there is illustrated an irradiation device 150 as a fifth alternative embodiment according to this invention. The irradiation device 150 comprises a balloon catheter 151 (hereinafter the catheter 151), a guide wire 195, a push tube 175 and a radiation source 185.

The catheter 151 is a flexible elongated tube 154 including a distal end portion 152, a distal end 155, a proximal end portion 153 and a passageway or lumen 157 with a diameter 158 extending longitudinally therebetween. The diameter 158 can remain constant along the length of the catheter 151. Accordingly, a difference between the irradiation device 150 and the embodiments of earlier Figures is that the catheter 151 does not have a partially closed distal end. The catheter 151 can also include a series of vents 159, a balloon 170 and a luer fitting 171. In this embodiment, the catheter 151 and/or the guide wire 195 are the carriers of the radiation source 185.

The guide wire 195 is a flexible elongated rod or tube (e.g., a wire is shown in FIG. 7) having a distal end portion 196 and a proximal end portion 197. From the proximal end portion 197 to just proximal to the distal end portion 196, the guide wire 195 can have a constant diameter 198. The distal end portion 196 can include an enlarged bulbous end having at its largest cross section, a diameter 199. Moreover, the diameter at any point in the distal end portion 196 is larger than the diameter 198. In addition, the diameter 198 of the guide wire 195 is smaller than the diameter 158 of the lumen 157. Accordingly, the guide wire 195 can be placed in the catheter 151 either before or after the catheter 151 has been inserted into the vascular pathway.

Another difference between the irradiation device 150 and the embodiments of earlier Figures is that the catheter 151 and/or the guide wire 195 are placed in a different location in order to expose the stenosis site to the radiation source 185.

The catheter 151 and the guide wire 195 are located such that the portion of the guide wire 195 just proximal to the distal end portion 196 is located at the stenosis site. In this way, when the radiation source 185 is moved past the distal end 155 and impeded by the distal end portion 196, the radiation source 185 is within the stenosis site.

Prior to beginning the irradiation procedure, the guide wire 195 can be inserted into the luer fitting 171. The physician can use the proximal end portion 197 to maneuver the distal end portion 196 through a distal end 155 of the catheter 151. Once the guide wire 195 is in place with its distal end portion 196 located within or through the distal end 155, the guide wire 195, along with the catheter 151, can function to deliver and house the radiation source 185 at a point proximal to the distal end portion 196.

In an alternative embodiment according to this invention, the diameter 199 of the distal end portion 196 of the guide wire 195 can be larger than the diameter 158 of the lumen 157. In this case, the guide wire 195 is placed in the vascular pathway before the catheter 151. The catheter 151 is then inserted over the guide wire 195 for movement to the stenosis site. Also, in an alternative embodiment according to this invention, the distal end portion 196 need not be circular in shape but can be any shape, so long as the cross section at any point of the distal end portion 196 is constructed to impede the movement of the radiation source 185 past the distal end 155.

The radiation source 185 is a sleeve which can have an inner diameter 189 that is larger than the diameter 198 of the guide wire 195 just proximal to the distal end portion 196. The radiation source also has a lumen 190 with a diameter equivalent to the inner diameter 189 of the radiation source 185. In addition, the radiation source 185 can have an outer diameter 188 which is smaller than the diameter 158 of the lumen 157. The sleeve-type radiation source 185 can be placed on and encircle the guide wire 195. In addition, the radiation source 185 can be constructed according to any of the alternative embodiments described as to the radiation sources 85 (FIG. 4) and 135 (FIGS. 5, 5A and 6). The radiation source 185 can be placed on the guide wire 195 either before or after the guide wire 195 is inserted into the catheter 151.

The radiation source 185 has a distal end 186 and a proximal end 187. The proximal end 187 of the source 185 interacts with a distal end 176 of the push tube 175 in the same way as the distal end 136 interacts with the distal end 126 (of FIGS. 5 and 5A). However, in this embodiment, the distal end 186 of the radiation source 185 can move past the distal end 155 of the catheter 151. The distal end 186 is impeded by the distal end portion 196 of the guide wire 195 because the diameter 198 of the distal end portion 196 is larger than the inner diameter 189 of the radiation source 185. Accordingly, the distal end portion 196 is the impediment which prevents the radiation source 185 from moving past the guide wire 196. Moreover, the stenosis site is exposed to the radiation source 185 by moving such source 185 past the distal end 155 and into the vascular pathway at the site.

The push tube 175 has the distal end 176 and a proximal end portion 177. Also, the push tube 175 has an outer diameter 179 and the inner diameter 178 sufficiently proportioned to fit within the space between the lumen 157 of the catheter 151 and the outer diameter of the guide wire 195 proximal to the bulbous distal end portion 196. The push tube 175 is constructed to abut the cross section of the proximal end 187 without slipping over the radiation source 185 or inside the lumen 190. In this way, the push tube 175 can translate a mechanical force applied to its proximal end portion 177 in the distal direction to the radiation source 185. Accordingly, the push tube 175 can interact with the radiation source 185 to advance the radiation source 185 to the distal end portion 152.

The push tube 175 can be placed over the guide wire 195 either before or after inserting the guide wire 195 into the catheter 151 (and either before or after the radiation source 185 is in place on the guide wire 195 (e.g., the radiation source 185 can be added last where it is in the form of a wrap around sleeve). Once the push tube 175 and the radiation source 185 are in place, a force can be applied to the push tube 175 to cause it to abut and then move the radiation source 185 to the stenosis site.

Referring to FIG. 7A, there is an alternative embodiment of the irradiation device 150 according to this invention. A push wire 175a can be a wire having a diameter small enough to fit in the space between the lumen 157 of the catheter 151 and the outer diameter of the guide wire 195 at any point around the circumference of the outer wall of the guide wire 195 proximal to the distal end portion 196. In this embodiment, the guide wire 195 can also act to impede the push wire 175a from passing through the lumen 190 (shown in FIG. 7) of the radiation source 185. In this way, the guide wire 195 assists the push wire 175a in translating a force applied in the distal direction to the radiation source 185 in order to advance the radiation source 185. In addition, the push wire 175a has a diameter that is sufficiently large to abut the radiation source 185 without passing over or under the radiation source 185. The push wire 175a includes a distal end 176a, which interacts with the radiation source 185 in the same manner as the distal end 176 of the push tube 175. Accordingly, the push wire 175a functions and is used in the same manner as the push tube 175 described above for FIG. 7.

Referring to FIG. 8, in an alternative embodiment of the irradiation device 150 according to this invention, a hydraulic force can be used to deliver the radiation source 185 to the stenosis site. For example, an injection of saline solution can be applied to the lumen 157 of the catheter 151 at the luer fitting 171 after the radiation source 185 has been inserted in the catheter 151. The hydraulic force of the injected saline solution on the proximal end 187 causes the radiation source 185 to move to the stenosis site. Moreover, the solution for applying the hydraulic force can exit the catheter 151 at the vents 159 and the aperture in the distal end 155. This is because the construction of each of the catheter 151 and the guide wire 195 is controlled to allow the fluid to exit the distal end 155 of the catheter 151 while allowing the guide wire 195 to impede the radiation source 185 from moving past the distal end 155. The solution used to apply the hydraulic force may be the same as that described above for FIG. 3.

As to the parts of the irradiation device 150 which are not specifically described regarding FIG. 8, they are equivalent to the embodiments of FIGS. 7 and 7A as to their functions and manner of use (including any alternative embodiments of any part of the device 150 of FIGS. 7 or 7A, including the addition of the push tube 175 or push wire 175a to combine a mechanical force with the hydraulic force).

Referring to FIG. 9, there is illustrated an irradiation device 200 as a seventh alternative embodiment according to this invention. The irradiation device 200 comprises a balloon catheter 211 (hereinafter, the catheter 211), a guide wire 245, a push tube 225 and a radiation source 235. In this embodiment, the catheter 211 and/or the guide wire 245 are carriers for the radiation source 235.

The catheter 211 is a flexible elongated tube 214 including a distal end portion 212, a proximal end portion 213 and a passageway or lumen 217 having a diameter 218 extending longitudinally therebetween. The diameter 218 can remain constant along the length of the catheter 211. The catheter 211 also has an outside diameter 219. In addition, the distal end portion 212 has a distal end 215.

The guide wire 245 is a flexible elongated wire having a distal end portion 246 and a proximal end portion 247. The guide wire 245 can have a constant diameter 248. The distal end portion 246 can include an enlarged bulbous end, having, at its largest cross section, a diameter 249. Moreover, the diameter at any point in the distal end portion 246 is larger than the diameter 248. In addition, while the diameter 248 of the guide wire 245 is smaller than the diameter 218 of the lumen 217, the diameter 249 is larger than the diameter 218. Accordingly, the guide wire 245 is in place before the catheter 211 is inserted onto the guide wire 245.

A difference between the irradiation device 200 and prior embodiments of FIGS. 7 to 8 is that the radiation source 235, which is a sleeve, is placed on and encircles the outside of the catheter 211. The radiation source 235 is a sleeve having an inner diameter 239 and an outer diameter 238. The inner diameter 239 that is larger than the outer diameter 219 of the catheter 211 smaller than the diameter 249 of the distal end portion 246 of the guide wire 245. The radiation source 235 can be closed sleeve (as shown in FIG. 9) which is placed on and encircles the catheter 211. In addition, the irradiation source 235 can be constructed according to any of the alternative embodiments described as to the radiation sources 85 and 135 (of FIGS. 4 and 6).

With the catheter in place over the guide wire 245 such that the distal end portion 212 is at the treatment site, the radiation source 235 can be placed on the proximal end portion 213 of the catheter. In an alternative embodiment, the radiation source 235 can be placed on the catheter before the catheter 211 is inserted into the vascular pathway.

The push tube 225 is a flexible elongated tube having an inner diameter 228 which is larger than the outer diameter 219 of the catheter 211 and smaller than the outer diameter 238 of the radiation source 235. The push tube 225 also has a distal end 226 and a proximal end portion 227. The push tube 225 can be placed over the catheter 211 after the catheter 211 is in place and either before or after the radiation source 235 is in place on the catheter 211 (e.g., the radiation source 235 can be added last where it is in the form of a wraparound sleeve). In an alternative embodiment, the push tube 225 can be placed on the catheter 211 before the catheter 211 is inserted into the vascular pathway (in this embodiment, the radiation source 235 can also be in place on the catheter 211 prior to insertion).

The push tube 225 is constructed to abut the cross section of a proximal end 237 of the radiation source 235 without slipping over the radiation source 235. In this way, the push tube 225 can translate a mechanical force applied to it in the distal direction to the radiation source 235. Accordingly, the push tube 225 can interact with the radiation source 235 to advance the radiation source 235 to the distal end portion 212.

The proximal end 237 of the radiation source 235 interacts with a distal end 226 of the push tube 225 in the same way as the distal end 136 interacts with the distal end 126 (of FIGS. 5 and 5A). However, in this embodiment, a distal end 236 of the radiation source 235 can move past the distal end 215 of the catheter 211. The distal end 236 is impeded by the distal end portion 246 of the guide wire 245 because the diameter 249 of the distal end portion 246 is larger than the inner diameter 239 of the radiation source 235. Accordingly, the distal end portion 246 impedes the radiation source 235 from moving past the distal end 215 of the catheter 211. Where the radiation source 235 is in place at the distal end portion 212, the stenosis site is exposed to radiation.

In an alternative embodiment according to this invention, the distal end portion 196 need not be circular in shape but can be in any shape, so long as the cross section at any point of the distal end portion 186 is constructed to impede the movement of the radiation source 196 past the distal end 155.

Referring generally to the embodiments of our invention, the radiation sources 85, 135, 185 and 235, like the radiation source 35, may be composed of any type of radiation presently known or hereinafter discovered. The examples of radiation sources for the radiation source 35 apply to the radiation sources 85, 135, 185 and 235 as well. In addition, each of the alternative embodiments of the irradiation devises 10, 50, 100, 150 and 200 may include the catheter 11, 51, 111, 151 and 211 without the balloon 20, 70, 120 and 170, respectively, and may function in the same manner as the catheter 11 without a balloon as described in FIG. 1. Moreover, the carriers used in this invention are not limited to catheters and/or guide wires; rather, any flexible elongated tubes, wires or other devices presently known or hereinafter discovered which are suitable for irradiation procedures and for the delivery or housing functions of this invention are contemplated as within the present invention.

Having thus described the present invention, it is to be understood that the above-described device embodiments are illustrative of the principals of this invention and that other device embodiments may be devised by those skilled in the art, without departing from the spirit and scope of the invention. Accordingly, the invention is not limited by the specific examples illustrated herein, but by the appended claims. In addition, combining parts of the different embodiments of this invention, i.e., the irradiation devices 10, 50, 100, 150, 200, is contemplated as within the scope of this invention. For example, a part of an irradiation device (or an alternative embodiment described for such part) of a given Figure may be combined with a part of another Figure in order to construct an irradiation device according to the principals of this invention.

What is claimed is:

1. An irradiation device for providing radiation treatment to a stenosed region of an artery, comprising:
   a flexible elongated tube having a proximal end portion, a distal end portion, and a lumen extending longitudinally therebetween, said distal end portion being sufficiently flexible to be guided through the vascular system;
   a radiation source free of attachment to said tube and being movable within said lumen; and
   an elongated flexible member wherein said elongated flexible member is capable of pushing said radiation source within said lumen
   wherein said radiation source is not integrated with said elongated flexible member.

2. The irradiation device of claim 1 wherein said lumen having a cross section and said tube further comprising a protrusion which decreases the cross section of said lumen so that said protrusion impedes the movement of said radiation source beyond said protrusion.

3. The irradiation device of claim 1 wherein said distal end portion of said tube further comprising a partially closed distal end and said distal end impedes the movement of said radiation source beyond said distal end.

4. The irradiation device of claim 1 wherein said radiation source is a solid pellet.

5. The irradiation device of claim 1 wherein said radiation source is a sleeve or spiral.

6. The irradiation device of claim 1 wherein said radiation source is a radioactive material adapted to form a partial sleeve.

7. The irradiation device of claim 1 wherein said elongated flexible member is a push wire.

8. The irradiation device of claim 1 wherein said elongated flexible member is a push sheath.

9. An irradiation device for providing radiation treatment to a stenosed region of an artery, comprising:
   a flexible elongated tube having an inner surface, a proximal end portion, a distal end portion, and a lumen extending longitudinally therebetween, said distal end portion being insertable into a body pathway;
   a flexible elongated support having an outer surface and a distal end portion and said support being insertable into said tube so that said inner surface of said tube and said outer surface of said support form concentric rings;
   a radiation source free of permanent attachment to said tube or said support and being movable on said support; and
   an elongated flexible member for applying a force to said radiation source for moving said radiation source on said support;
   wherein said radiation source is not integrated with said elongated flexible member.

10. The irradiation device of claim 9 wherein:
    said radiation source having a cross section;
    said distal end portion of said flexible elongated support further comprising a distal end having a cross section larger than said cross section of said radiation source; and
    said distal end of said support impedes the movement of said radiation source beyond said distal end.

11. The irradiation device of claim 9 wherein:
    said lumen having a cross section;
    said tube further comprising a protrusion which decreases the cross section of said lumen;
    said support movable within said tube so that said support is placed in proximity to said protrusion; and
    wherein the combination of said protrusion and said support impedes the movement of said radiation sleeve beyond said protrusion.

12. The irradiation device of claim 9 wherein:
    said distal end portion of said tube further comprising a partially closed distal end;
    said support movable within said tube so that said support is placed in proximity to said distal end of said tube; and
    wherein the combination of said distal end of said tube and said support impedes the movement of said radiation source beyond said distal end of said tube.

13. The irradiation device of claim 9 wherein said radiation source is a sleeve.

14. The irradiation device of claim 9 wherein said radiation source is a radioactive material adapted to be at least partially wrapped around said support.

15. The irradiation device of claim 9 wherein said flexible elongated support is a wire.

16. The irradiation device of claim 9 wherein said flexible elongated support is a tube.

17. The irradiation device of claim 9 wherein said elongated flexible member is a push wire.

18. The irradiation device of claim 9 wherein said elongated flexible member is a push sheath.

* * * * *